United States Patent
Rohan et al.

(10) Patent No.: US 7,033,312 B2
(45) Date of Patent: *Apr. 25, 2006

(54) MAGNETIC FIELD STIMULATION TECHNIQUES

(75) Inventors: Michael L. Rohan, Cambridge, MA (US); Aimee Parow, Allston, MA (US); Perry F. Renshaw, Arlington, MA (US)

(73) Assignee: McLean Hospital Corporation, Belmont, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 10/452,947

(22) Filed: Jun. 2, 2003

(65) Prior Publication Data

US 2004/0010177 A1 Jan. 15, 2004

Related U.S. Application Data

(63) Continuation of application No. 09/839,258, filed on Apr. 20, 2001, now Pat. No. 6,572,528.

(51) Int. Cl.
*A61N 1/00* (2006.01)

(52) U.S. Cl. ....................................................... 600/14

(58) Field of Classification Search .............. 600/9–15, 600/373, 547, 549; 607/3, 34, 41, 66, 72, 607/99–102, 113, 148
See application file for complete search history.

(56) References Cited

U.S. PATENT DOCUMENTS

| | | | | |
|---|---|---|---|---|
| 4,428,366 A * | 1/1984 | Findl et al. | .................... | 600/14 |
| 5,441,495 A * | 8/1995 | Liboff et al. | .................. | 600/13 |
| 5,620,463 A * | 4/1997 | Drolet | ............................ | 607/3 |
| 5,725,471 A | 3/1998 | Davey et al. | .................. | 600/13 |
| 5,769,778 A | 6/1998 | Abrams et al. | ................ | 600/14 |
| 5,813,970 A * | 9/1998 | Abrams et al. | ................ | 600/14 |
| 5,833,600 A * | 11/1998 | Young | ......................... | 600/300 |
| 6,029,090 A * | 2/2000 | Herbst | .......................... | 607/66 |
| 6,086,525 A | 7/2000 | Davey et al. | .................. | 600/13 |
| 6,132,361 A * | 10/2000 | Epstein et al. | ................ | 600/13 |
| 6,155,966 A * | 12/2000 | Parker | .......................... | 600/13 |
| 6,161,048 A * | 12/2000 | Sluijter et al. | .............. | 607/100 |
| 6,198,958 B1 * | 3/2001 | Ives et al. | .................... | 600/411 |
| 6,366,813 B1 * | 4/2002 | DiLorenzo | .................... | 607/45 |
| 6,402,678 B1 * | 6/2002 | Fischell et al. | ................ | 600/13 |
| 6,491,620 B1 * | 12/2002 | Davey | ............................ | 600/9 |
| 6,572,528 B1 * | 6/2003 | Rohan et al. | .................. | 600/14 |

FOREIGN PATENT DOCUMENTS

WO  WO 98/06342  2/1998

OTHER PUBLICATIONS

T.A. Kimbrell et al., "Frequency Dependence Of Antidepressant Response To Left Prefrontal Repetitive Transcranial Magnetic Stimulation (rTMS) As A Function Of Baseline Cerebral Glucose Metabolism," *Biol. Psychiatry*, 46: 1603-1613 (1999).

(Continued)

*Primary Examiner*—Samuel G. Gilbert
(74) *Attorney, Agent, or Firm*—Fish & Richardson P.C.

(57) ABSTRACT

The invention involves enhancing brain function by stimulating the brain using magnetic fields. Applications of the new methods include improving the condition of individuals with cognitive disorders, such as depression, and studying the effects of neural stimulation using induced electric fields. These techniques can avoid deleterious effects of psychotropic pharmaceutical treatments, and provide a relatively safe, comfortable, inexpensive means of direct cranial stimulation.

30 Claims, 4 Drawing Sheets

OTHER PUBLICATIONS

H.M. Kolbinger et al., "Transcranial Magnetic Stimulation (TMS) In The Treatment Of Major Depression—A Pilot Study," *Human Psychopharmacology*, vol. 10: 305-310 (1995).

S.H. Lisanby et al., "Magnetic Seizure Therapy Of Major Depression," *Arch Gen Psychiatry*, vol. 58: 303-304 (2001).

S.H. Lisanby et al., "Sham TMS: Intracerebral Measurement Of The Induced Electrical Field And The Induction Of Motor-Evoked Potentials," *Biol. Psychiatry*,49: 460-463 (2001).

C. Loo et al., "Effects Of A 2- To 4-Week Course Of Repetitive Transcranial Magnetic Stimulation (rTMS) On Neuropsychologic Functioning, Electroencephalogram, And Auditory Threshold In Depressed Patients," *Biol. Psychiatry*, 49:615-623 (2001).

K.A. McConnell, "The Transcranial Magnetic Stimulation Motor Threshold Depends On The Distance From Coil To Underlying Cortex: A Replication In Healthy Adults Comparing Two Methods Of Assessing The Distance To Cortex," *Biol. Psychiatry*, 49:454-459 (2001).

J.F. Rosenbaum et al., "Vagus Nerve Stimulation For Treatment-Resistant Depression," *Biol. Psychiatry*, 47:273-275 (2000).

B.J. Roth et al., "A Theoretical Calculation Of The Electric Field Induced In The Cortex During Magnetic Stimulation," *Electroencephalography and Clinical Neurophysiology*, 81:47-56 (1991).

A. Pascual-Leone et al., "Rapid-Rate Transcranial Magnetic Stimulation Of Left Dorsolateral Prefrontal Cortex In Drug-Resistant Depression," *The Lancet*, 348: 233-237 (Jul. 1996).

H.A. Sackeim, "Repetitive Transcranial Magnetic Stimulation: What Are The Next Steps?," *Biol. Psychiatry*, 48:959-961 (2000).

G.J. Siegle et al., "Pupillary And Reaction Time Measures Of Sustained Processing Of Negative Information In Depression," *Biol. Psychiatry*, (2001).

N.YA. Stikhina et al., "Transcranial Magnetic Stimulation In Neurotic Depression," 10:26-29 (1999) (translation provided).

W.J. Triggs et al., "Improving Brain Function With Transcranial Magnetic Stimulation?" *Neurology*, 56:429-430 (2001).

E.M. Wasserman, "Risk And Safety Of Repetitive Transcranial Magnetic Stimulation: Report And Suggested Guidelines From The International Workshop On The Safety Of Repetitive Transcranial Magnetic Stimulation," *Electroencephalography and Clinical Neurophysiology*, 108:1-16 (1998).

T. Zyss et al., "The Magnetic Brain Stimulation In Treatment Of Depression: The Search For The Perfect Stimulus," *Psychiatria Polska*, 4:611-628 (1996).

T. Zyss et al., "The Behavioral And Biochemical Effects Of The Magnetic Brain Stimulation And Electroconvulsive Shocks In Rats," *Psychiatria Polska*, 4:593-610 (1996).

"Substitute For Shock Therapy?" *Science*, 270:1409-1540 (1995).

B. Boroojerdi et al., "Enhancing Analogic Reasoning With RTMS Over The Left Prefrontal Cortex," *Neurology*, 56:526-528 (2001).

L.G. Cohen et al., "Effects Of Coil Design On Delivery Of Focal Magnetic Stimulation. Technical Considerations," *Electroencephalography and Clinical Neurophysiology*, 75:350-357 (1990).

P. Collins, "The Field Workers," *New Scientist*, No. 2224:36-39 (Feb. 2000).

R. Cracco et al., "Cerebral Function Revealed By Transcranial Magnetic Stimulation," *J. Neuroscience Methods*, 86:209-219 (1999).

V. Di Lazzaro et al., "Comparison Of Descending Volleys Evoked By Transcranial Magnetic And Electric Stimulation In Conscious Humans," *Electroencephalography and Clinical Neurophysiology*, 109:397-401 (1998).

O.T. Dolberg et al., "Transcranial Magnetic Stimulation-Induced Switch Into Mania: A Report Of Two Cases," *Biol. Psychiatry*., 49:468-470 (2001).

G.W. Eschweiler et al., "Left Prefrontal Activation Predicts Therapeutic Effects Of Repetitive Transcranial Magnetic Stimulation (rTMS) In Major Depression," *Psychiatry Research*,Neuroimaging Section 99:161-172 (2000).

M.S. George et al., "Transcranial Magnetic Stimulation: A Neuropsychiatric Tool For The 21$^{st}$ Century," *J. Neuropsychiatry*, vol. 8, No. 4: 373-382 (1996).

M.S. George et al., "A Controlled Trial Of Daily Left Prefrontal Cortex TMS For Treating Depression," *Biol. Psychiatry*, 48:962-970 (2000).

M. Hallett, "Transcranial Magnetic Stimulation And The Human Brain," *Nature*, 406: 147-150 (Jul. 2000).

A. Hausmann et al., "Chronic Repetitive Transcranial Magnetic Stimulation Enhances c—fos In The Parietal Cortex and Hippocampus," *Molecular Brain Research*, 76:355-362 (2000).

M.E. Keck et al., "Neuroendocrine And Behavioral Effects Of Repetitive Transcranial Magnetic Stimulation In A Psychopathological Animal Model Are Suggestive Of Antidepressant-Like Effects," *Neuropsychopharmacology*, vol. 24, No. 4: 337-349 (2001).

* cited by examiner

FIG. 1
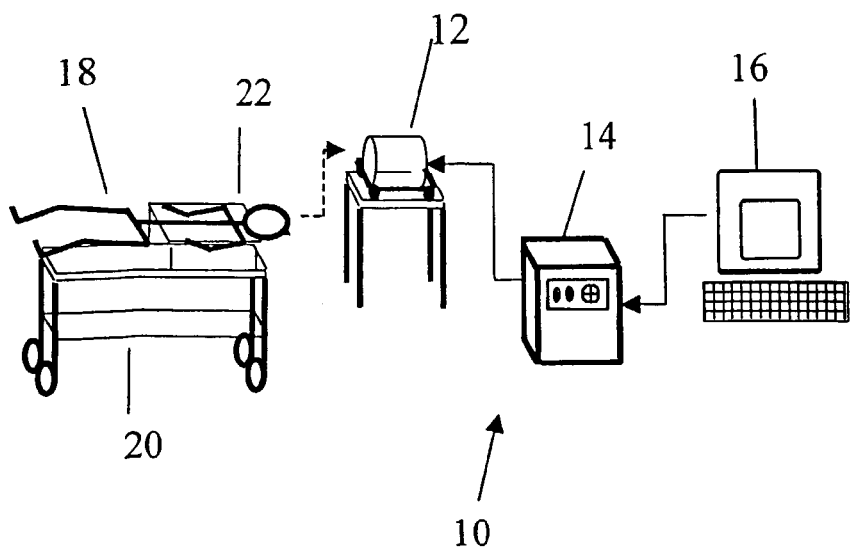
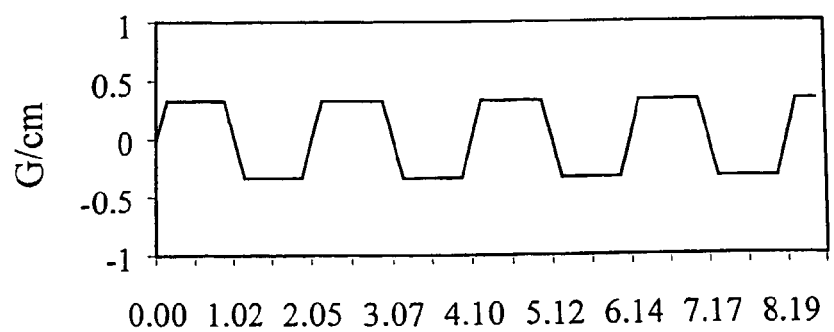
FIG. 2    milliseconds
FIG. 3
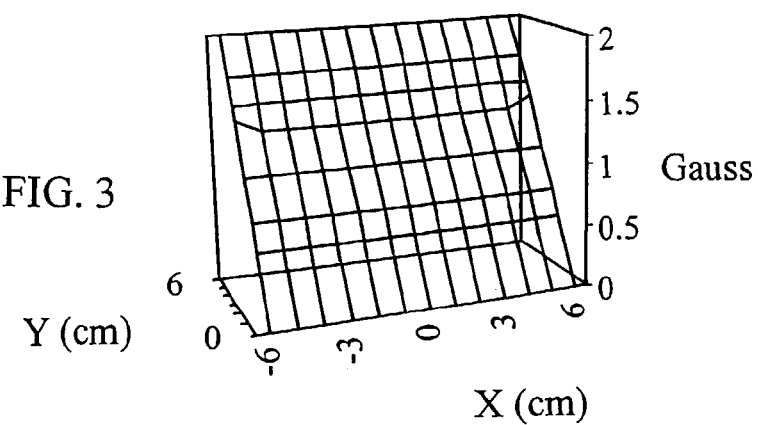

| Mood Change | Total visits | Lithium | Valproic Acid | Topiramate | Quetiapine | Unmedicated |
|---|---|---|---|---|---|---|
| Improved | 22 | 3 | 9 | 0 | 2 | 7 |
| No change | 18 | 4 | 10 | 2 | 1 | 1 |
| Worse | 3 | 1 | 1 | 0 | 0 | 1 |
| Total visits | 43 | 8 | 20 | 2 | 3 | 9 |
FIG. 7
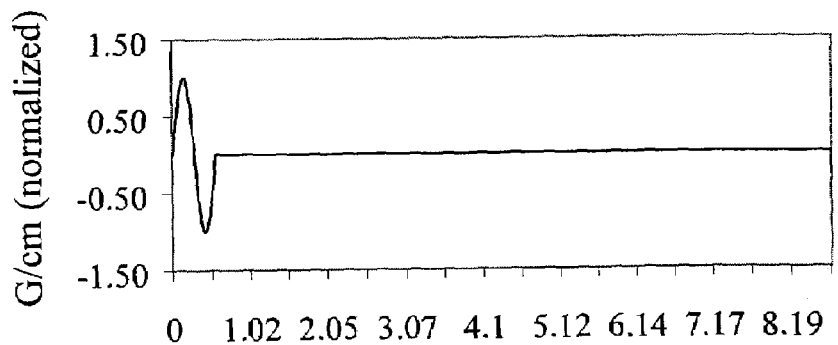
FIG. 8
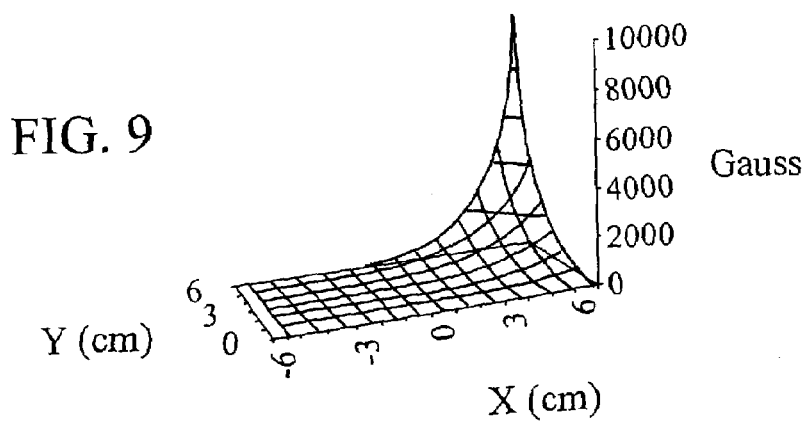
FIG. 9

MAGNETIC FIELD STIMULATION TECHNIQUES

CROSS-REFERENCE TO RELATED APPLICATIONS

This application is a continuation of incorporates by reference U.S. patent application Ser. No. 09/839,258, filed Apr. 20, 2001, which now is U.S. Pat. No. 6,572,528.

TECHNICAL FIELD

This invention relates to magnetic stimulation techniques, and more particularly to neural stimulation using a magnetic field.

BACKGROUND

Repetitive transcranial magnetic stimulation (rTMS) has been used with the goal of treating depression, see, e.g., George et al., *The Journal of Neuropsychiatry and Clinical Neurosciences*, 8:373, 1996; Kolbinger et al., *Human Psychopharmacology*, 10:305, 1995.

One example of an rTMS technique uses a figure-8 surface coil with loops that are 4 cm in diameter (Cadwell, Kennewick, Wash.). This coil is placed next to the scalp, and is usually positioned to direct the magnetic field at the prefrontal cortex of the brain, see, e.g., George et al., *The Journal of Neuropsychiatry and Clinical Neurosciences*, 8:373, 1996. An electric current is run through the magnetic coil to generate a magnetic field, specifically a sequence of single-cycle sinusoidal pulses where each pulse has a frequency of approximately 1800 Hz (or about 560 microseconds per pulse). These pulses are delivered at a repetition rate of 1 to 20 Hz (i.e., one pulse every 0.05 to 1 second), see, e.g., George et al, *Biological Psychiatry*, 48:962, 2000; Eschweiler et al, *Psychiatry Research: Neuroimaging Section*, 99:161, 2000.

Some subjects have declined participation in rTMS studies due to pain induced in the scalp. In addition, seizures have been reported as a result of rTMS treatment, see, George et al, *Biological Psychiatry*, 48:962, 2000; Wasserman, *Electroencephalography and Clinical Neurophysiology* 108:1, 1998.

SUMMARY

The invention concerns enhancing brain function using novel magnetic field techniques. These magnetic field techniques use low field strengths, high repetition rates, and uniform gradients to improve brain function.

In one aspect of the present invention, a subject is selected for enhancement of brain function using a magnetic field. The subject's head is then subjected to a time-varying magnetic field having a maximum strength of less than about 50 G.

Advantages of this aspect of the invention include the following. Subjects with cognitive impairments may benefit from the new treatment by the lessening of the severity of the condition. Treatment techniques using this method can be administered inexpensively with relative safety and comfort, and offer a substitute for or complement to treatment by medication. Applications of the new methods include improving the condition of individuals with cognitive disorders, such as depression, and studying the effects of brain stimulation using induced electric fields.

Embodiments of this aspect of the invention can include one or more of the following features. After treating the subject (e.g., a human patient), the subject can be evaluated for enhanced brain function. The magnetic field can have a maximum strength of less than about 10 G. The field can also be a gradient magnetic field that is substantially uniform (i.e., a magnetic field one or more of whose x, y, or z direction components varies approximately linearly in space; that is, has a constant gradient to within, e.g., 10%) and unidirectional over the relevant volume (e.g., the entire brain, or a region of interest of the brain such as the prefrontal cortex). The gradient of the magnetic field can be less than about 5 G/cm. The magnetic field can be generated using a sequence of trapezoidal pulses of alternating polarity, where each pulse has a duration of about 1 millisecond.

In another aspect of the present invention, a subject is selected for enhancement of brain function using a magnetic field. The subject's head is then subjected to a time-varying gradient magnetic field that is substantially uniform and unidirectional.

In another aspect of the present invention, a subject is selected for enhancement of brain function using a magnetic field. The subject's head is then subjected to a time-varying magnetic field generating by a sequence of pulses, each having a duration of less than about 10 milliseconds.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a diagram of a system and apparatus for administering the present magnetic field treatments.

FIG. 2 is an example of a magnetic field waveform used in the present magnetic field treatment methods.

FIG. 3 is a three-dimensional plot of a magnetic field used in the present magnetic field treatment methods.

FIG. 7 is a table of the effects of the present treatment on the mood of twenty-one depressed subjects over forty-three visits, sorted by medication.

FIG. 8 is an example of a magnetic field waveform used in an example of repetitive transcranial magnetic stimulation.

FIG. 9 is a three-dimensional plot of a magnetic field used in an example of repetitive transcranial magnetic stimulation.

DETAILED DESCRIPTION

Apparatuses and Systems

Figure 4:
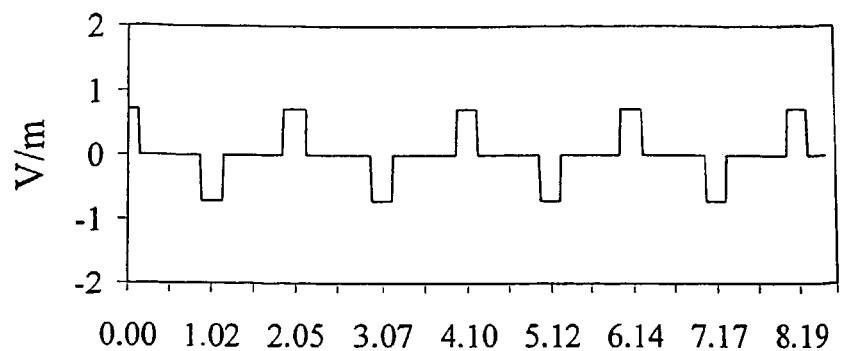
FIG. 4 is an example of an electric field waveform induced using the present magnetic field treatment methods.

A device 10 according to the present invention is shown in FIG. 1. The device 10 has a magnetic coil 12, an amplifier 14, and a waveform generator 16. The waveform generator 16 (e.g., a general-purpose programmable computer or a purpose-built electric circuit) provides an electrical pulse sequence to the amplifier 14, which amplifies the electrical signals and provides them to the magnetic coil 12.

The magnetic coil 12 produces a magnetic field in response to electrical signals received from the amplifier 14. Over the region in which the subject's brain is positioned, the magnetic field is a gradient magnetic field that is substantially uniform (i.e., the magnetic field strength varies substantially linearly in only one direction, e.g., at about 5 G/cm, with the variation occurring from anterior to posterior across the subject's head) and unidirectional (i.e., the vectors representing the magnetic field all point in substantially the same direction, e.g., along the long axis of the subject's body). (Alternatively, a magnetic coil can be used that generates a substantially uniform and unidirectional gradient magnetic field over only a region of interest of the brain, e.g., the left prefrontal cortex.) The magnetic coil 12 is large enough to accommodate a subject's head, with a diameter of, e.g., about 35 cm (14 in.).

When being treated with device 10, the subject 18 lays down on a standard patient gurney 20 with a head support 22, with his or her head positioned inside the coil 12.

Other devices can also be used for administering the present treatment method. For instance, a conventional magnetic resonance imaging apparatus can be used. Alternatively, instead of using a device such as device 10 that consists of separate components, the device can instead integrate one or more components, e.g., to make the device easily portable. Alternatively or additionally, the magnetic coil can be included in a hat-like structure, and the waveform generator, amplifier, and power source (e.g., a battery) integrated into a control mechanism that the subject carries or wears, i.e., on his or her subject's belt. The subject can self-administer the treatment, and the treatment can be applied while the subject is lying down, standing, sitting, or in motion. Alternatively or additionally, the control device can be pre-set to administer the treatment for specific periods at specific intervals or continuously.

Methods

Prior to receiving treatment using device 10, a subject is selected as a candidate for enhancement of brain function. This selection is generally performed by medical professionals, e.g., because the subject has been diagnosed as suffering a cognitive impairment. Alternatively, a subject could self-select based on a perceived need or desire to enhance brain function. Selection can be based on either subjective or objective criteria, including, e.g., anxiety, moodiness, depression, lethargy, sleepiness, learning difficulties, and memory impairments.

To administer the treatment, the subject's head is positioned inside coil 12, and subjected to a time-varying magnetic field. (Alternatively, the subject's entire body could be positioned inside a full-body coil, and subjected to a magnetic field.)

The magnetic pulse train used to generate the time-varying magnetic field is shown in FIG. 2. The pulse train comprises a sequence of pulses delivered at a high rate. As discussed in detail below, the magnetic field induces an electrical field in the subject's brain. This electrical field can interact with neurons to cause cognitive effect. In light of this, the duration of each individual magnetic pulse is selected to be on the order of the refractory period of an axon, i.e., on the order of several milliseconds (e.g., 1 to 10 milliseconds), see, e.g., E. R Kandel et al., *Principles of Neural Science*, 1991, which is incorporated by reference herein. Thus, the pulse duration can be from on the order of 0.5 milliseconds to 10 milliseconds.

For example, each pulse has a trapezoidal shape, with 128 microsecond ramp times (from zero to plateau) and 768 microsecond plateau times (for a total duration of 1.024 milliseconds). The pulses alternate in polarity, with a short gap between successive pulses. A single pulse train comprises 512 successive pulses, and so lasts for about a half-second. After a delay of about a second-and-a-half, the pulse train is repeated (giving one pulse train every two seconds), and the treatment concludes after about six hundred repetitions (for a total treatment time of about 20 minutes). Alternatively, the second-and-a-half delay between successive pulse trains can be eliminated.

At the plateau of each trapezoidal pulse, the maximum magnetic field strength is on the order of 5–10 G, with a magnetic field gradient of 0.33 G/cm. FIG. 3 shows a three-dimensional plot of the resultant magnetic field. Pulse sequences yielding maximum magnetic field strengths of up to about 50 G, and maximum magnetic field gradients of up to about 5 G/cm, can alternatively be used.

These magnetic fields induce electric fields in the subject's brain. The characteristics of these electric fields are defined by the magnetic field parameters according to Maxwell's equation: $\nabla \times E(x, y, z, t) = -\partial B(x, y, z, t)/\partial t$, where $\nabla \times E$ is the curl of the electric field and $$\frac{\partial B}{\partial t}$$

is the rate of change of the magnetic field over time. In Cartesian coordinates, this equation becomes:

$$\partial E_x/\partial y - \partial E_y/\partial x = -\partial B_z/\partial t,$$

$$\partial E_y/\partial z - \partial E_z/\partial y = -\partial B_x/\partial t,$$

$$\partial E_z/\partial x - \partial E_x/\partial z = -\partial B_y/\partial t,$$

where the subscripts x, y, and z denote the component of the fields along those respective axes, see, e.g., J. D. Jackson, *Classical Electrodynamics*, 1975, which is incorporated herein by reference.

These equations describe fields in free space (i.e., fields produced in the absence of other material). When conductive matter, such as brain tissue, is placed in the changing magnetic field, a charge distribution is also induced, resulting in an electric field. This electric field will affect the overall electric field in the head. This charge distribution can alter the free space electric field by up to about 50%, see Roth et al, *Electroencephalography and Clinical Neurophysiology*, 81:47, 1991, which is incorporated herein by reference. The pattern of the effect of the charge distribution will depend on the shape and placement of the subject's head.

Two local field distributions are of particular interest. In the first, the z-component (superior-inferior component) of the magnetic field has a uniform gradient in the y-direction (anterior-posterior direction), and the y-component has a uniform gradient in the z-direction: ($B_x=0$, $B_y=G(t)z$, $B_z=G(t)y$), where G(t) is the value of the gradient. In this case, the electric field is given by:

$$\left(E_x = E_0(t) + \frac{1}{2}(\partial G(t)/\partial t) \cdot (y^2 - z^2), E_y = 0, E_z = 0\right),$$

where $E_0(t)$ is a spatially constant field term that depends on the size of the coil and, consequently, the extent of the magnetic field. The preceding field description applies equally for the two other orientations, which is obtained by replacement of x with y, y with z, and z with x or by replacement of x with z, y with x and z with y, in both the vector components and coordinates. In addition, a given vector combination of these three field components, which forms an equivalent but rotated field, is also appropriate. Thus, one approach to applying the new treatment techniques involves using a magnetic field that has a vector component with a gradient that is substantially uniform, e.g., to within 10%, in value or direction over a relevant volume of the subject's brain, e.g., a 8 cm³ volume or the left prefrontal cortex.

In another magnetic field distribution, the magnetic field is uniform over a local volume, which can be expressed as: ($B_x=0$, $B_y=0$, $B_z=B(t)$). The corresponding local electric field is: ($E_x=E_0(t)-a(\partial B(t)/\partial t)\cdot y$, $E_y=E_0(t)-(1-a)(\partial B(t)/\partial t)\cdot y$, $E_z0$), where a is an arbitrary parameter determined by the details of coil winding.

In both situations, if $E_0(t)$ is sufficiently large compared to $\partial G(t)/\partial t \cdot R^2$ or $\partial B(t)/\partial t \cdot R$, where R is an effective radius of the volume of interest, e.g., the radius of a subject's brain, then the local electric field is substantially uniform. The preceding field description applies equally for other orientations and rotations.

FIG. 4 shows the electric field waveform induced in the subject's brain when subjected to the magnetic field waveform shown in FIG. 2. The electric field waveform is a sequence of alternating monophasic square pulses of alternating polarity. The width of each induced electric pulse corresponds to the ramping period for the magnetic field pulses, i.e., 256 microseconds. For the 0.33 G/cm magnetic field pulse amplitude, the electric field amplitude is approximately 0.7 V/m. This electric field strength is approximately an order of magnitude less than the minimum peripheral nerve stimulation threshold of approximately 6–25 V/m, see, e.g., J. P. Reilly, *Medical and Biological Engineering and Computing*, 27:101, 1989, thus providing an appropriate margin of safety against causing pain or seizures in the patient.

Figure 5:
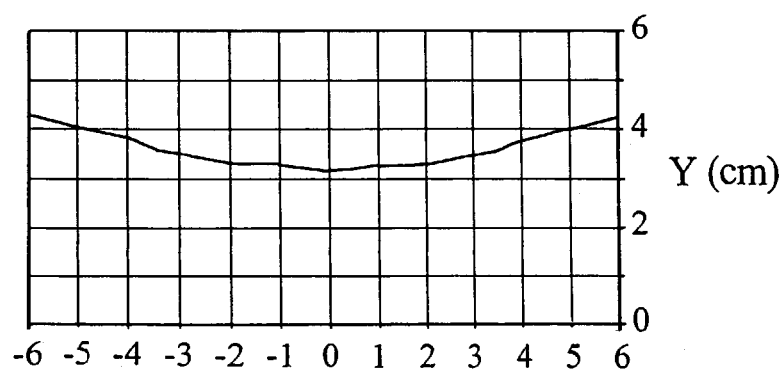
FIG. 5 is a contour plot of an electric field used in the present magnetic field treatment methods.
Figure 6:
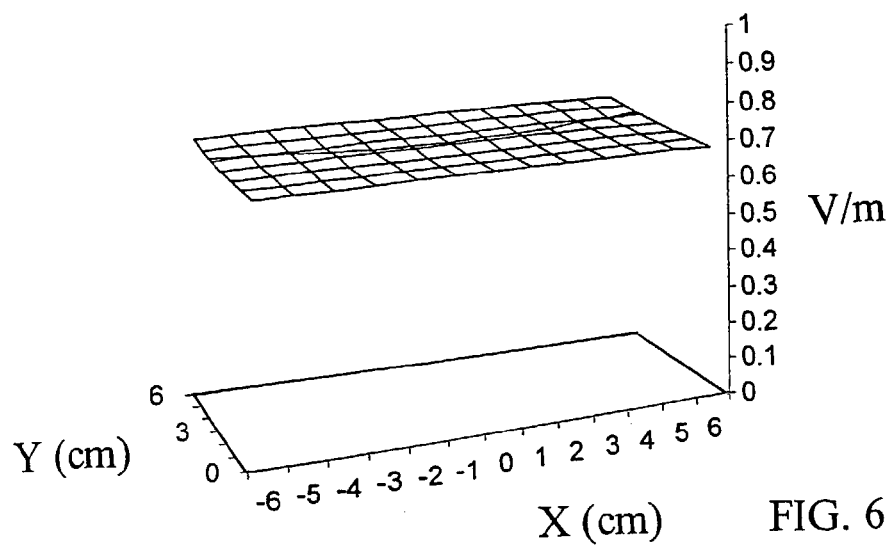
FIG. 6 is a three-dimensional plot of an electric field used in the present magnetic field treatment methods.

FIGS. 5 and 6 are contour and three-dimension plots of this electric field, respectively. These plots were made by modeling with Biot-Savart style integration, see, e.g., J. D. Jackson, *Classical Electrodynamics*, 1975, which is incorporated herein by reference, for free space values using a magnetic field with a vector component having a gradient that is substantially uniform in value and direction. The plots in FIGS. 5 and 6 show that the electric field is substantially uniform in direction and changes slowly with distance. The direction of the induced electric field is determined by Maxwell's equations. For a magnetic field that has a gradient oriented from anterior to posterior across the subject's head, the induced electric field is oriented in from right to left across the subject's head.

EXAMPLES

Experiment

Twenty-one people exhibiting symptoms of depression were selected by medical professionals and subjected to the present method. Twelve subjects reported a post-treatment overall mood improvement of at least one point on the Brief Affect Scale, which involves asking a subject to rate his mood after treatment compared to his mood at an earlier time, using a seven point scale: (1) very much improved, (2) much improved, (3) minimally improved, (4) no change, (5) minimally worse, (6) much worse, (7) very much worse. The results for forty-three visits by the twenty subjects are given in the table in FIG. 7. As reflected in FIG. 7, the effects of the treatment on unmedicated subjects were most prevalent, with unmedicated subjects demonstrating mood improvement after seven of nine visits. This demonstrates that the new treatment is useful both as a substitute for and complement to drug therapy. The effects can be substantial; four subjects reported a pronounced, sustained improvement that lasted over a week. There were three reports by patients of mood worsening.

The treatments were administered using a General Electric 1.5T Sigma MRI scanner. After optional water suppression, slice selective excitation, and a spatial phase encoding pulse, the device applied a train of 512 trapezoidal alternating-polarity magnetic field pulses. These pulses were about one millisecond long, with ramp times of 128 microseconds and 768 microsecond plateau times. During the plateau of each pulse, the gradient was 0.33 G/cm, and the maximum magnetic field in the cortex was about 5 G. The entire train of 512 pulses was repeated every 2 seconds, six hundred times, for a total treatment time of 20 minutes. FIG. 3 is a three-dimensional plot of this magnetic field, and FIG. 2 is a diagram of the pulse train. The 'Y' gradient coil in the magnetic resonance scanner, having an approximate diameter of about 90 cm (36 in.), was used to apply this sequence, orienting the gradient in the anterior-posterior direction for the supine subjects. The gradient of the z-component of the magnetic field from this coil in the y-direction is uniform in both magnitude and direction over a subject's brain to within about 5%.

The magnetic field induced an electric field in the brains of the subjects. This electric field was oriented from right to left, from the subject's perspective, and had a magnitude of approximately 0.7 V/m. FIGS. 5 and 6 respectively show contour and three-dimension plots of this electric field modeled for free space values using a wire pattern for a coil similar to the 'Y' gradient coil in the Signa MRI system and computed with Biot-Savart style integration. The induced electric field consisted of 256 microsecond monophasic square pulses, where each pulse has a single polarity and an amplitude of approximately 0.72 V/m. A diagram of this electric field waveform is shown in FIG. 4. To achieve the same electric field with a smaller coil, Maxwell's equations show that a higher magnetic field is needed. Using a coil with a similar shape but smaller diameter, e.g., a "head-sized" 35 cm (14 in.) coil instead of a 36-inch "whole-body"

gradient coil, to induce a similar same electric field magnitude would employ a magnetic field that reaches approximately 50 G in the head. The magnetic field used to induce such an electric field can have a vector component with a gradient that is slightly less uniform in value and direction, varying by about 10% over the cranial volume. In addition, a higher magnetic field, e.g., 100 G, can be used with a smaller coil that provides a vector component with a substantially uniform gradient over only a region, e.g. 8 cm$^3$, of the brain.

COMPARATIVE EXAMPLE

One example of an rTMS technique uses a figure-8 surface coil with loops that are 4 cm in diameter (Cadwell, Kennewick, Wash.). This coil is placed next to the scalp, and is usually positioned to direct the magnetic field at the prefrontal cortex of the brain, see, e.g., George et al., *The Journal of Neuropsychiatry and Clinical Neurosciences*, 8:373, 1996. An electric current is run through the magnetic coil to generate a magnetic field, specifically a sequence of single-cycle sinusoidal pulses where each pulse has a frequency of approximately 1800 Hz (or about 560 microseconds per pulse). These pulses are delivered at a repetition rate of 1 Hz (i.e., one single-cycle sinusoidal pulse every 1 second), see, e.g., George et al, *Biological Psychiatry*, 48:962, 2000; Eschweiler et al, *Psychiatry Research: Neuroimaging Section*, 99:161, 2000. This waveform is shown in FIG. 8. As the repetition period is much longer than the time span on the x-axis, only one single-cycle sinusoidal pulse appears in FIG. 8.

The magnetic field generated by the FIG. 8 waveform is shown in FIG. 9. The field reaches its maximum strength of approximately 10,000 G at the face of the coil. The strength of this magnetic field decreases rapidly as the distance from the coil increases, to about 0 G at about 6 cm to 8 cm, see, e.g., Cohen et al, *Electroencephalography and Clinical Neurophysiology*, 75:350, 1990.

Figure 10:
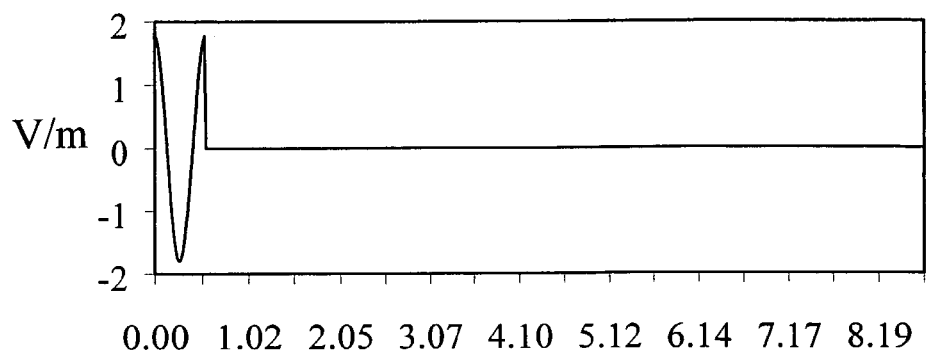
FIG. 10 is an example of an electric field waveform induced using an example of repetitive transcranial magnetic stimulation.

FIG. 10 shows the electric field waveform induced in the subject's brain by the magnetic field shown in FIG. 9. This waveform consists of a series of 560-microsecond single-cycle cosine pulses that repeat every 1 Hz.

Figure 11:
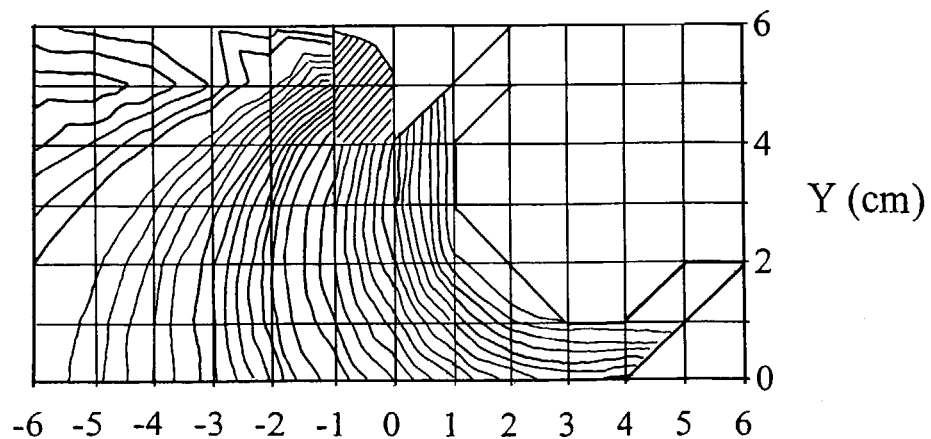
FIG. 11 is a contour plot of an electric field used in an example of repetitive transcranial magnetic stimulation.
Figure 12:
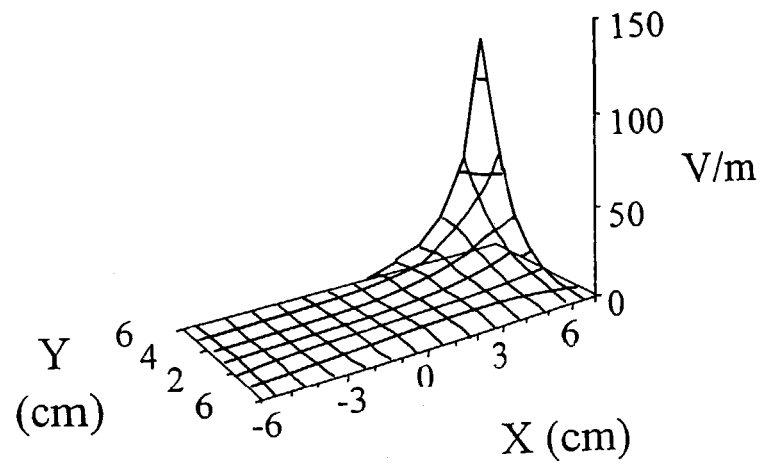
FIG. 12 is a three-dimensional plot of an electric field used in an example of repetitive transcranial magnetic stimulation.

FIG. 11 shows the contour plot and FIG. 12 shows the three-dimensional plot of the electric field induced in free space by the magnetic field shown in FIG. 2A. The electric field is approximately 120 V/m at the face of the coil, and falls to about 0.02 V/m on the side of the head opposite the coil. The contours of this rapidly diminishing electric field reflect the shape of the figure-8 surface coil with 4 cm diameter loops, tilted at 45°, and placed 6.7 cm vertically and horizontally from a position equivalent to the center of the head: the electric field forms roughly circular loops.

A number of embodiments of the invention have been described. Nevertheless, it will be understood that various modifications may be made without departing from the spirit and scope of the invention. Accordingly, other embodiments are within the scope of the following claims.

What is claimed is:

1. A method of enhancing brain function, comprising:
    (a) selecting a subject for enhancement of brain function using a magnetic field;
    (b) generating a time-varying magnetic field, wherein the magnetic field induces an electric field in air comprising a series of electric pulses, wherein the pulses have a duration less than about 10 milliseconds, and wherein each pulse has a single polarity and the pulses are separated by periods of substantially no electric field; and
    (c) subjecting the subject's head to the time-varying magnetic field.

2. The method of claim 1, further comprising:
    (d) evaluating the subject for enhanced brain function after subjecting the subject to the magnetic field.

3. The method of claim 1, wherein the subject is human.

4. The method of claim 1, wherein selecting a subject involves identifying a subject showing symptoms of anxiety, depression, or an affective disorder.

5. The method of claim 1, wherein the electric pulses have an amplitude less than about 5 V/m.

6. The method of claim 1, wherein the electric field is substantially unidirectional over at least a region of the brain.

7. The method of claim 1, wherein successive electric pulses have alternating polarity.

8. The method of claim 1, wherein the duration of each electric pulse in the series is less than or equal to about 1 millisecond.

9. The method of claim 1, wherein the frequency of the series of electric pulses is about 1 kHz.

10. The method of claim 1, wherein the electric field magnitude is substantially spatially uniform over the subject's brain.

11. The method of claim 1, wherein the magnetic field has a maximum strength of less than about 50 G.

12. A method of enhancing brain function, comprising:
    (a) selecting a subject for enhancement of brain function using a magnetic field;
    (b) generating a time-varying magnetic field, wherein the magnetic field induces an electric field in air comprising a series of electric pulses, wherein the series of pulses has a frequency of at least about 100 Hz, and wherein each pulse has a single polarity and the pulses are and separated by periods of substantially no electric field; and
    (c) subjecting the subject's head to the time-varying magnetic field.

13. The method of claim 12, wherein the subject is human.

14. The method of claim 12, wherein selecting a subject involves identifying a subject showing symptoms of anxiety, depression, or an affective disorder.

15. The method of claim 12, wherein the electric pulses have an amplitude less than about 5 V/m.

16. The method of claim 12, wherein the electric field is substantially unidirectional over at least a region of the brain.

17. The method of claim 12, wherein successive electric pulses have alternating polarity.

18. The method of claim 12, wherein the electric field magnitude is substantially spatially uniform over the subject's brain.

19. The method of claim 12, wherein the series of pulses have a frequency of about 1 kHz.

20. The method of claim 12, further comprising:
    (d) evaluating the subject for enhanced brain function after subjecting the subject to the magnetic field.

21. A method of enhancing brain function, comprising:
    (a) selecting a subject for enhancement of brain function using a magnetic field;
    (b) generating a time-varying magnetic field, wherein the magnetic field induces an electric field in air comprising a series of electric pulses, wherein the electric field is substantially unidirectional over at least a region of the brain, and wherein each electric pulse has a single polarity and the pulses are and separated by periods of substantially no electric field; and (c) subjecting the subject's head to the time-varying magnetic field.

22. The method of claim 21, wherein selecting a subject involves identifying a subject showing symptoms of anxiety, depression, or an affective disorder.

23. The method of claim 21, wherein the electric pulses have an amplitude less than about 5 V/m.

24. The method of claim 21, wherein the region is an interior region of the brain.

25. The method of claim 21, wherein the region is a prefrontal cortex.

26. The method of claim 21, wherein the unidirectional electric field is oriented from one ear of the subject's head to the other ear of the subject's head.

27. The method of claim 21, wherein successive electric pulses have alternating polarity.

28. The method of claim 21, wherein the electric field magnitude is substantially spatially uniform over the subject's brain.

29. The method of claim 21, further comprising:

(d) evaluating the subject for enhanced brain function after subjecting the subject to the magnetic field.

30. The method of claim 21, wherein the subject is human.

* * * * *